(12) United States Patent
Gish

(10) Patent No.: US 11,879,245 B2
(45) Date of Patent: Jan. 23, 2024

(54) PORTABLE WATER NOISE MAKER DEVICE

(71) Applicant: Hillary Gish, Millbrook, AL (US)

(72) Inventor: Hillary Gish, Millbrook, AL (US)

(*) Notice: Subject to any disclaimer, the term of this patent is extended or adjusted under 35 U.S.C. 154(b) by 831 days.

(21) Appl. No.: 16/932,700

(22) Filed: Jul. 17, 2020

(65) Prior Publication Data

US 2022/0018107 A1 Jan. 20, 2022

(51) Int. Cl.
*E03D 9/14* (2006.01)
*A61M 21/02* (2006.01)
*A61M 21/00* (2006.01)
*A47K 13/24* (2006.01)
*G11B 9/00* (2006.01)

(52) U.S. Cl.
CPC ............... *E03D 9/14* (2013.01); *A47K 13/24* (2013.01); *A61M 21/02* (2013.01); *G11B 9/00* (2013.01); *A61M 2021/0027* (2013.01); *E03D 2201/00* (2013.01)

(58) Field of Classification Search
CPC ....... E03D 9/14; E03D 2201/00; A47K 13/24; A61M 21/02; A61M 2021/0027; G11B 9/00

See application file for complete search history.

(56) References Cited

U.S. PATENT DOCUMENTS

| | | | | |
|---|---|---|---|---|
| 2003/0185401 A1* | 10/2003 | Watson | ................. | H04R 27/00 381/73.1 |
| 2014/0224518 A1* | 8/2014 | Snidow | .................... | H02G 3/18 174/60 |
| 2015/0359993 A1* | 12/2015 | Samar | .................... | A61M 21/02 434/236 |

\* cited by examiner

*Primary Examiner* — Michael C Zarroli
(74) *Attorney, Agent, or Firm* — Lyman Moulton, Esq.; Moulton Patents, PLLC

(57) ABSTRACT

The disclosure includes a water sounds noise maker and wall mount for inducing urination. The noise maker is battery powered, and mounts to the wall for convenience or may be worn or mounted by other means. Battery power sources include but are not limited to power sources which are rechargeable, plug-in and solar powered options. The invention contains three settings for duration of sounds, three options for sounds, and volume control. The disclosure manages inducing urination for clients by recording and playing various water sounds. Various prerecorded water noises from sources outside a housing of the disclosure, are also reproduced to induce urination.

16 Claims, 5 Drawing Sheets

Front view

Back view

Front view

Back view

PORTABLE WATER NOISE MAKER DEVICE

BACKGROUND OF THE INVENTION

Field of Invention

The present invention relates to a portable battery powered water noise maker machine with the purpose of facilitating urination.

Description of Related Art

Background noise or ambient noise is any sound other than the sound being monitored. Background noises include environmental noises such as water waves, traffic noise, alarms, extraneous speech, noise from animals, and electrical noise from devices such as refrigerators, air conditioning, power supplies, and motors.

While many people struggle to use the restroom, they find that running the faucet helps to facilitate urination. In an effort to alleviate water being wasted and make the process easier for those disabled, noise making machines are the better choice.

Many portable noise maker machines are currently on the market, sold by various retailers such as Walmart, Target, Bed Bath & Beyond, Amazon, Kohl's, and more. These devices contain different sounds, such as white noise, ocean waves, thunder, rain, stream, or summer night, and a variety of other features. However, the purpose of these devices is to facilitate sleep or calmness in the listener. The object of the present invention is to provide a water noises making device to aid anyone in their efforts to urinate.

DETAILED DESCRIPTION

The present invention is a water sounds device with an adhesive wall mount. The Urinaid is sleek and simple in design, complements any decor. It has either a plastic or steel shell, or any high durometer material depending on its application.

The term 'battery,' in the present disclosure, refers to a power source including but not limited to power sources which are rechargeable, plug-in and solar powered options.

Figure 1:
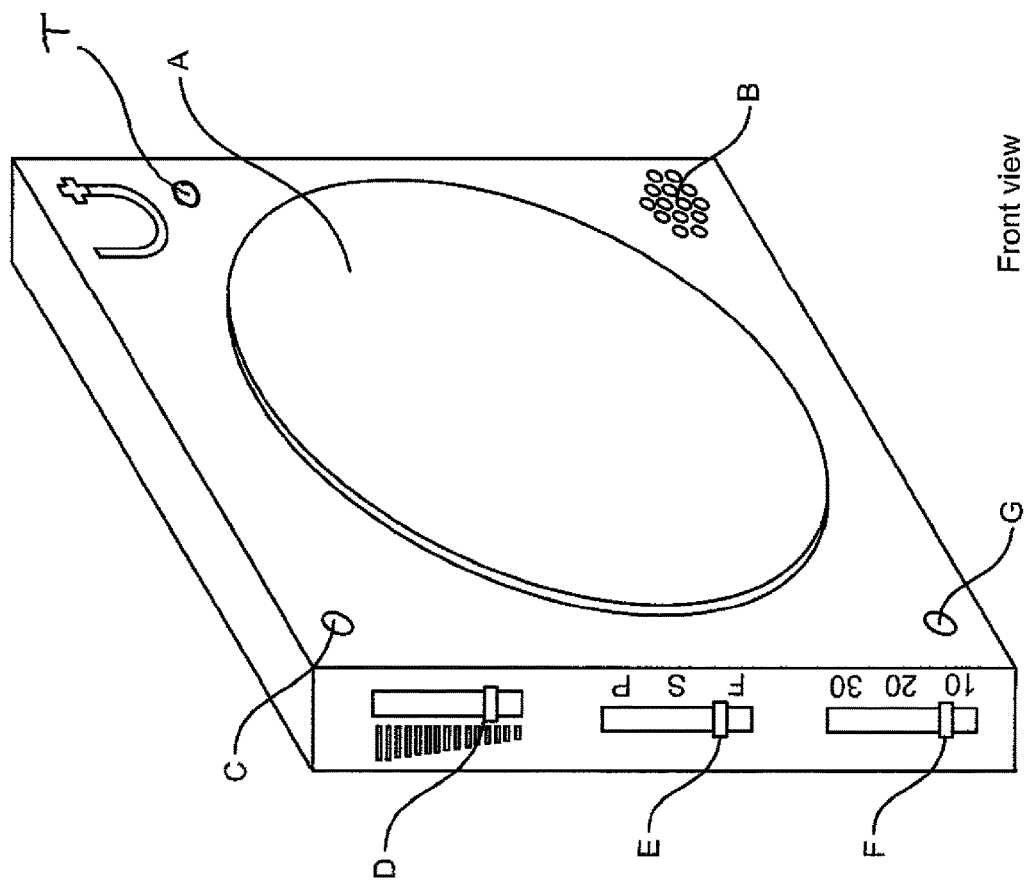
FIG. 1 depicts the front view of the sound device in accordance with an embodiment of the present disclosure.

FIG. 1 depicts the front view of the sound device in accordance with an embodiment of the present disclosure. On the left edge or side panel of the device is a sliding scale for volume control D, a sliding scale selection bar E for sound selection control including three options generated by a digital signal processor including fast F, slow S and real time play P, and a sliding scale to control time duration selection, including three time options of 10, 20, and 30 seconds. The front panel includes the button A as a primary mechanical trigger of reproducing recorded audio of urination, flushing toilet and hand washing where the button is large enough to be pressed by a person's elbow, the speaker B, a motion sensor C, an auxiliary port G such as to use the device with headphones, and a motion sensor C. The motion sensor C allows for an experience of the disclosure via a hands free trigger of the disclosure to limit spreading of bacteria. The built-in speaker emits crisp sound at specified volume, and the aux port allows user to plug in for a more private experience. The mechanical button T acts as a secondary button to A and controls an audio recording of urination, flushing toilet and hand washing.

Figure 2:
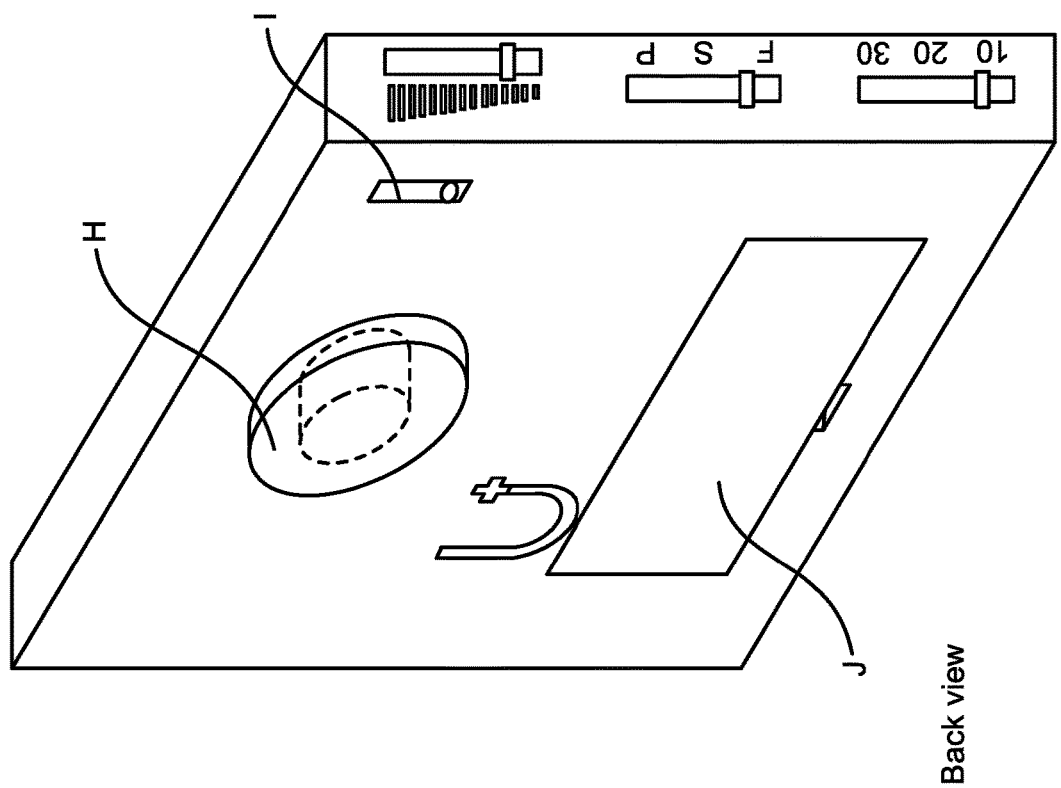
FIG. 2 depicts the back view or wall facing side of the sound device in accordance with an embodiment of the present disclosure.

FIG. 2 depicts the back view of the sound device in accordance with an embodiment of the present disclosure. The unit includes a mounting knob H to secure the device to the wall mount, an on/off switch I for the motion sensor C of FIG. 1 and a battery compartment J.

Figure 3:
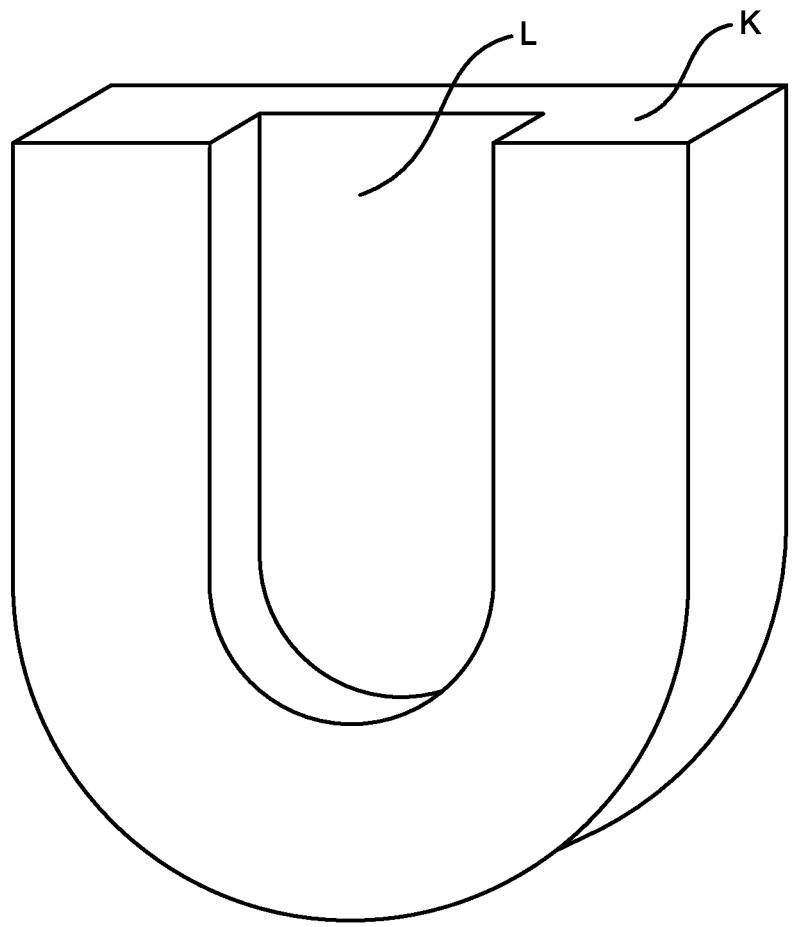
FIG. 3 depicts the front view of a wall mount in accordance with an embodiment of the present disclosure.

FIG. 3 depicts the front view of a wall mount clip K in accordance with an embodiment of the present disclosure. The mount includes a slot L for the knob on the sound system to slide in and be held in place.

Figure 4:
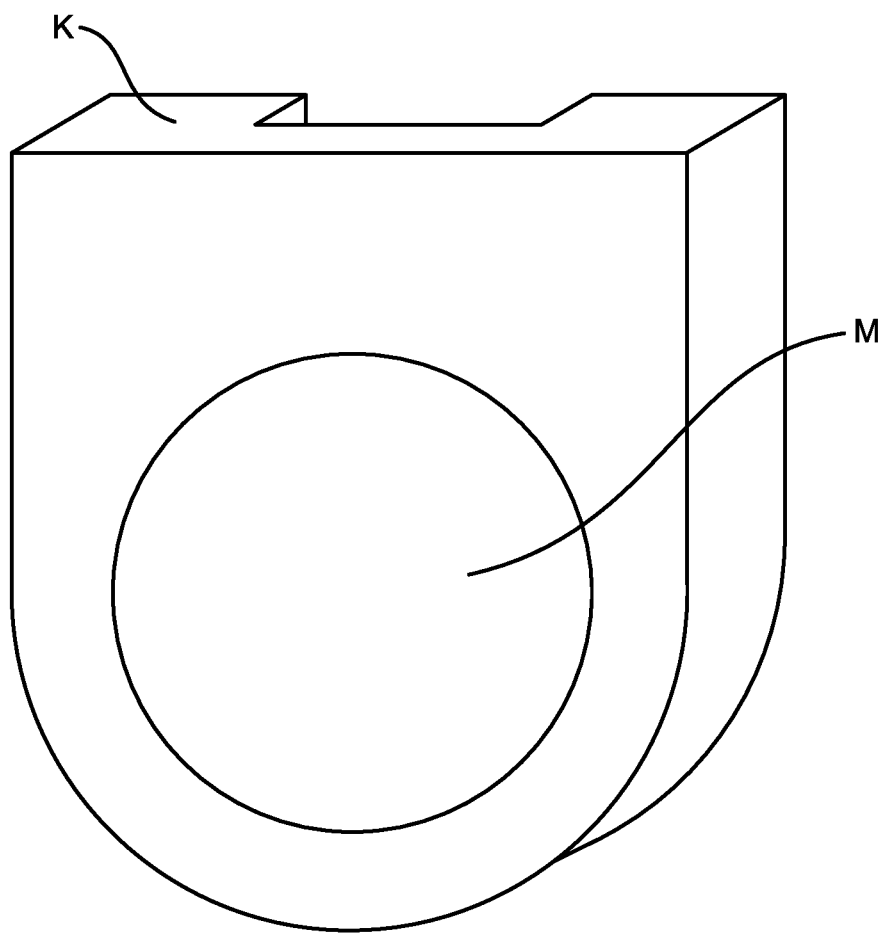
FIG. 4 depicts the back view or wall facing side of a wall mount in accordance with an embodiment of the present disclosure.

FIG. 4 depicts the back view of a wall mount K in accordance with an embodiment of the present disclosure. A large adhesive sticker M on the back of the wall mount holds the wall mount and sound system to the wall or desired vertical surface. The Urinaid attaches to any surface with the provided adhesive sticker, which removes cleanly without leaving a residue. Another option for attachment could be a hanging clip or a hook and latch style, also known as Velcro®.

Figure 5:
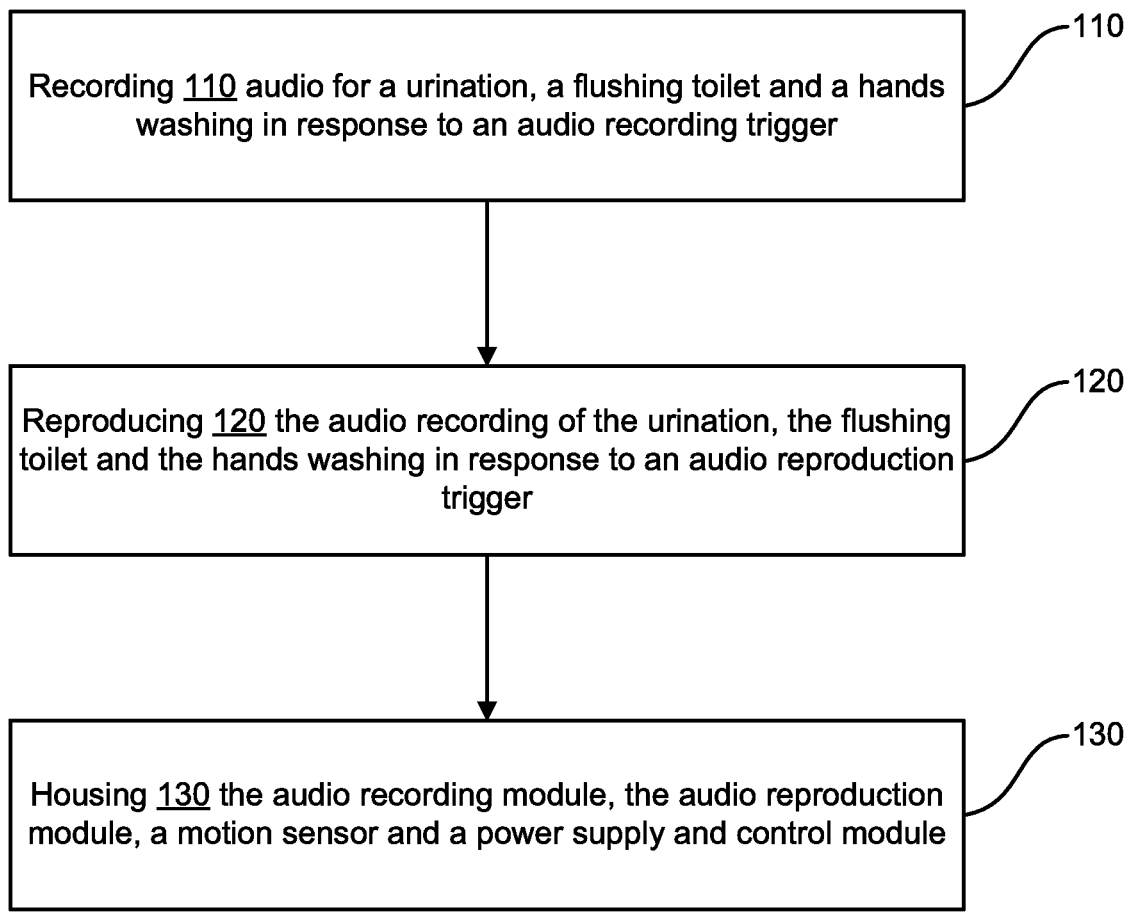
FIG. 5 depicts a flow chart of a method for inducing urination in accordance with an embodiment of the disclosure.

FIG. 5 depicts a flow chart of a method for inducing urination via audio reproduction in accordance with an embodiment of the disclosure. The audio reproduction method includes recording 110 audio for a urination, a flushing toilet and a hands washing in response to an audio recording trigger. The method also includes reproducing 120 the audio recording of the urination, the flushing toilet and the hands washing in response to an audio reproduction trigger. The method further includes housing 130 the audio recording module, the audio reproduction module, a motion sensor and a power supply and control module.

Pre-recorded sound options best for facilitating urination are a faucet running water, water pouring into water and natural water sources such as a babbling brook. Other water and liquid sounds suggestive to urination as recognized by those with ordinary skill in the art are included in embodiments of the present disclosure.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:

1. An audio reproduction device, comprising:
   a. an audio recording module configured to record audio for a urination, a flushing toilet and a hand washing in response to an audio recording trigger;
   b. an audio reproduction module configured to produce an audio reproduction of the recorded audio of the urination, the flushing toilet and the hands washing in response to an audio reproduction trigger;

c. a digital signal processor configured to generate a sliding scale sound selection bar including a fast, a slow and a real time play of the audio reproduction; and d. a housing for the audio recording module, the audio reproduction module, the digital signal processor and a power supply and control module, the housing comprising a wall mount and hanging clips.

2. The device of claim 1, further comprising a motion sensor configured to sense a motion within a predefined distance from the audio reproduction device and trigger the audio reproduction.

3. The device of claim 1, wherein the housing further comprises a primary mechanical push button configured to trigger the audio reproduction.

4. The device of claim 1, wherein the housing further comprises a secondary mechanical push button configured to trigger the audio recording.

5. The device of claim 1, wherein the audio reproduction module further comprises an audio speaker.

6. The device of claim 1, wherein the audio recording module further comprises an audio microphone.

7. The device of claim 1, wherein the wall mount comprises a post portion affixed to the housing and another portion configured adjacent to the post portion.

8. The device of claim 1, further comprising a sliding scale time duration for the audio reproduction including increments of 10 minutes.

9. The device of claim 1, wherein the housing further comprises a plurality of auxiliary ports for peripheral devices including headphones, a universal serial bus connection, an external microphone and auxiliary speakers.

10. An audio reproduction method, the method comprising:

a. recording audio for a urination, a flushing toilet and a hand washing in response to an audio recording trigger;

b. reproducing the audio recording of the urination, the flushing toilet and the hands washing in response to an audio reproduction trigger;

c. generating a sliding scale sound selection via a digital signal processor including a fast, a slow and a real time play of the audio reproduction; and d. housing the audio recording module, the audio reproduction module, the digital signal processor, a motion sensor and a power supply and control module.

11. The method of claim 10, further comprising sensing a motion within a predefined distance from the audio reproduction device to trigger the audio reproduction.

12. The device of claim 10, further comprising playing the audio reproduction via an audio speaker.

13. The device of claim 10, further comprising recording the audio recording via an audio microphone.

14. The device of claim 10, further comprising hanging the device by receiving a post portion affixed to a wall into a slot portion on the housing.

15. The method of claim 10, further comprising playing the audio reproduction via a sliding scale time duration in increments of 10 minutes.

16. The method of claim 10, further comprising storing a plurality of water noise prerecordings from sources outside the housing.

* * * * *